US010371646B2

(12) United States Patent
Boyer (10) Patent No.: US 10,371,646 B2
(45) Date of Patent: Aug. 6, 2019

(54) METHOD AND SYSTEM FOR AUTOMATED DATA COLLECTION AND PART VALIDATION

(71) Applicant: The Boeing Company, Chicago, IL (US)

(72) Inventor: Mark James Boyer, Placentia, CA (US)

(73) Assignee: The Boeing Company, Chicago, IL (US)

( * ) Notice: Subject to any disclaimer, the term of this patent is extended or adjusted under 35 U.S.C. 154(b) by 260 days.

(21) Appl. No.: 15/269,033

(22) Filed: Sep. 19, 2016

(65) Prior Publication Data
US 2018/0080882 A1    Mar. 22, 2018

(51) Int. Cl.
| G01N 21/00 | (2006.01) |
| G01N 21/95 | (2006.01) |
| B25J 18/02 | (2006.01) |
| B25J 9/00 | (2006.01) |
| B25J 9/04 | (2006.01) |

(52) U.S. Cl.
CPC ............ *G01N 21/95* (2013.01); *B25J 9/0018* (2013.01); *B25J 9/046* (2013.01); *B25J 18/025* (2013.01); *G01N 2201/06113* (2013.01); *G01N 2201/10* (2013.01); *Y10S 901/44* (2013.01); *Y10S 901/47* (2013.01)

(58) Field of Classification Search
USPC ................. 700/245–264; 901/41, 44, 46, 47
See application file for complete search history.

(56) References Cited

U.S. PATENT DOCUMENTS

| 4,118,220 A | * | 10/1978 | von Dreusche, Jr. ..... F23G 5/28 423/88 |
| 4,613,269 A | * | 9/1986 | Wilder ................... B25J 9/1697 348/92 |
| 4,615,729 A | * | 10/1986 | Victorovich .............. C22B 5/14 75/641 |
| 4,620,362 A | * | 11/1986 | Reynolds ................. B25J 15/04 279/900 |
| 4,706,324 A | * | 11/1987 | Goodspeed .......... D21C 11/122 15/246 |
| 5,041,907 A | * | 8/1991 | Sager .................... B07C 5/3422 348/91 |
| 5,237,468 A | * | 8/1993 | Ellis .......................... B25J 5/02 360/92.1 |
| 5,310,248 A | * | 5/1994 | King ....................... E21C 35/24 299/1.1 |
| 5,443,354 A | * | 8/1995 | Stone ...................... B25J 5/005 414/729 |

(Continued)

OTHER PUBLICATIONS

"FARO Laser Tracker—Laser Tracking Solutions," FARO Technologies, Inc., retrieved Aug. 1, 2016, 12 pages. http://www.faro.com/products/metrology/faro-laser-tracker/overview.

*Primary Examiner* — Jonathan L Sample
(74) *Attorney, Agent, or Firm* — Yee & Associates, P.C.

(57) ABSTRACT

An inspection system comprises a crane system, a six axis, one hundred and fifty degree articulating robotic arm, a laser inspection system, and a communications system. The robotic arm is connected to a base of the crane system. The laser inspection system is connected to the robotic arm. The communications system is configured to send and receive instructions for the crane system, the robotic arm, and the laser inspection system.

17 Claims, 6 Drawing Sheets

(56) References Cited

U.S. PATENT DOCUMENTS

| | | | | |
|---|---|---|---|---|
| 5,542,650 A * | 8/1996 | Abel | F27D 3/1527 | 15/246 |
| 5,912,403 A * | 6/1999 | Bilke | C21B 13/008 | 75/313 |
| 6,165,411 A * | 12/2000 | Adachi | B22D 17/007 | 164/312 |
| 6,579,091 B1 * | 6/2003 | Simonen | B08B 1/00 | 15/104.16 |
| 7,039,499 B1 * | 5/2006 | Nasr | B25J 9/046 | 206/710 |
| 7,327,869 B2 * | 2/2008 | Boyer | G05B 23/0216 | 382/141 |
| 7,409,263 B2 * | 8/2008 | Elliott | H01L 21/67379 | 700/213 |
| 7,765,780 B2 * | 8/2010 | Koselka | A01D 46/30 | 56/10.2 A |
| 7,784,348 B2 * | 8/2010 | Dubois | G10K 15/046 | 73/620 |
| 7,891,325 B2 * | 2/2011 | Koskela | F23J 1/08 | 110/182.5 |
| 8,930,042 B2 * | 1/2015 | Jang | G01N 29/225 | 701/2 |
| 9,020,636 B2 * | 4/2015 | Tadayon | B25J 5/02 | 700/247 |
| 9,873,230 B1 * | 1/2018 | DesJardien | B29C 70/388 | |
| 2001/0056313 A1 * | 12/2001 | Osborne, Jr. | A47G 21/08 | 700/245 |
| 2002/0181650 A1 * | 12/2002 | D'Ambrosio | G01N 23/04 | 378/43 |
| 2003/0212505 A1 * | 11/2003 | Rojas | C21C 5/4673 | 702/39 |
| 2003/0217706 A1 * | 11/2003 | Pingel | B08B 9/00 | 122/387 |
| 2004/0177722 A1 * | 9/2004 | Halpin | C22B 1/2406 | 75/303 |
| 2004/0179924 A1 * | 9/2004 | Lundahl | B65G 59/02 | 414/416.01 |
| 2005/0126144 A1 * | 6/2005 | Koselka | A01D 46/30 | 56/10.2 R |
| 2006/0101996 A1 * | 5/2006 | Paxton | B01D 47/00 | 95/87 |
| 2006/0218680 A1 * | 9/2006 | Bailey, III | B08B 1/00 | 414/217 |
| 2007/0000117 A1 * | 1/2007 | Brandstatter | C21B 1/673 | 29/527.2 |
| 2007/0006658 A1 * | 1/2007 | Kennedy | G01N 29/265 | 73/622 |
| 2007/0272130 A1 * | 11/2007 | Eriksson | D21C 11/122 | 110/182.5 |
| 2008/0087302 A1 * | 4/2008 | Koskela | F23J 1/06 | 134/22.11 |
| 2008/0282486 A1 * | 11/2008 | Pingel | F23J 1/02 | 15/104.063 |
| 2011/0169202 A1 * | 7/2011 | Rosner | F27D 3/04 | 266/135 |
| 2012/0145682 A1 * | 6/2012 | Yeum | B23K 26/032 | 219/121.63 |
| 2012/0152877 A1 * | 6/2012 | Tadayon | B25J 5/02 | 212/224 |
| 2012/0271501 A1 * | 10/2012 | Zhao | G03B 37/005 | 701/25 |
| 2013/0014600 A1 * | 1/2013 | Sarr | G01N 29/041 | 73/866.5 |
| 2013/0231777 A1 * | 9/2013 | Salamanca | B25J 11/00 | 700/245 |
| 2013/0261876 A1 * | 10/2013 | Froom | G01M 5/0016 | 701/29.3 |
| 2015/0032387 A1 * | 1/2015 | Froom | G01N 29/225 | 702/33 |
| 2015/0128717 A1 * | 5/2015 | May | G01N 21/95 | 73/800 |
| 2015/0134191 A1 * | 5/2015 | Kim | G01M 17/007 | 701/29.7 |
| 2015/0323501 A1 * | 11/2015 | Smith | G01N 27/902 | 700/245 |
| 2016/0011593 A1 * | 1/2016 | Oberoi | B29C 45/14336 | 701/23 |

* cited by examiner

METHOD AND SYSTEM FOR AUTOMATED DATA COLLECTION AND PART VALIDATION

BACKGROUND INFORMATION

1. Field

The present disclosure relates generally to inspecting parts and, more specifically, to inspecting parts using a laser inspection system. Still more particularly, the present disclosure relates to inspecting parts using a laser inspection system connected to a robotic arm connected to a base of a crane system.

2. Background

Currently, parts are validated for dimensional conformance using computer-aided metrology or physical inspection. Floor space dedicated to conventional computer-aided metrology equipment may be undesirably large.

Computer-aided metrology equipment has a dedicated location. The parts may be moved to the computer-aided metrology equipment for inspection within a manufacturing environment. Moving the parts to the computer-aided metrology equipment may take an undesirable amount of time or energy. Additionally, moving the parts may cause inconsistencies in the parts.

Dimensions of computer-aided metrology equipment limit an inspected part size. Some parts may be too large to fit within the conventional computer-aided metrology equipment. When the parts are too large to fit within the computer-aided metrology equipment, the parts may be physically inspected.

Physical inspection may be undesirably expensive due to a large amount of operator time. Further, the physical inspection may be less accurate than desired. Therefore, it would be desirable to have a method and apparatus that take into account at least some of the issues discussed above, as well as other possible issues.

SUMMARY

In one illustrative embodiment, an inspection system is presented. The inspection system comprises a crane system, a six axis, one hundred and fifty degree articulating robotic arm, a laser inspection system, and a communications system. The robotic arm is connected to a base of the crane system. The laser inspection system is connected to the robotic arm. The communications system is configured to send and receive instructions for the crane system, the robotic arm, and the laser inspection system.

In another illustrative embodiment, an inspection system is presented. The inspection system comprises a crane system, a telescoping arm, a six axis, one hundred and fifty degree articulating robotic arm, a laser inspection system, a wireless device, and a communications system. The crane system has a base and a track system. The base of the crane system travels in at least one of an x-direction or a y-direction in a manufacturing environment along the track system. The telescoping arm is connected to the base of the crane system. The six-axis, one hundred and fifty degree articulating robotic arm is connected to the telescoping arm. The laser inspection system is connected to the robotic arm. The wireless device is configured to activate movement at least one of the crane system, the telescoping arm, or the robotic arm for inspection of a structure within the manufacturing environment by the laser inspection system. The communications system is configured to send and receive instructions for the crane system, the robotic arm, and the laser inspection system.

In yet another illustrative embodiment, a method of inspecting a structure in a manufacturing environment is presented. A base of a crane system is driven within the manufacturing environment. A robotic arm connected to the base is moved relative to the base. The robotic arm is a six-axis, one hundred and fifty degree articulating robotic arm. Inspection data for the structure is formed using a laser inspection system connected to the robotic arm during at least one of driving the base of the crane system or moving the robotic arm.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The different illustrative embodiments recognize and take into account one or more different considerations. For example, the illustrative embodiments recognize and take into account that crane systems are present in aircraft manufacturing facilities. The crane systems in the aircraft manufacturing facilities are used to lift and move large components within the aircraft manufacturing facilities. The illustrative embodiments recognize and take into account that a crane system may be mounted to a ceiling of an aircraft manufacturing facility.

The illustrative embodiments recognize and take into account that the crane system is designed to move within the aircraft manufacturing facility without interfering with manufacturing operations. For example, the crane system may be elevated enough to avoid collisions with components in the aircraft manufacturing facility.

The illustrative embodiments further recognize and take into account that the crane system is designed to access a substantial portion of the aircraft manufacturing facility. In some examples, the crane system may access the majority of the aircraft manufacturing facility.

Figure 1:
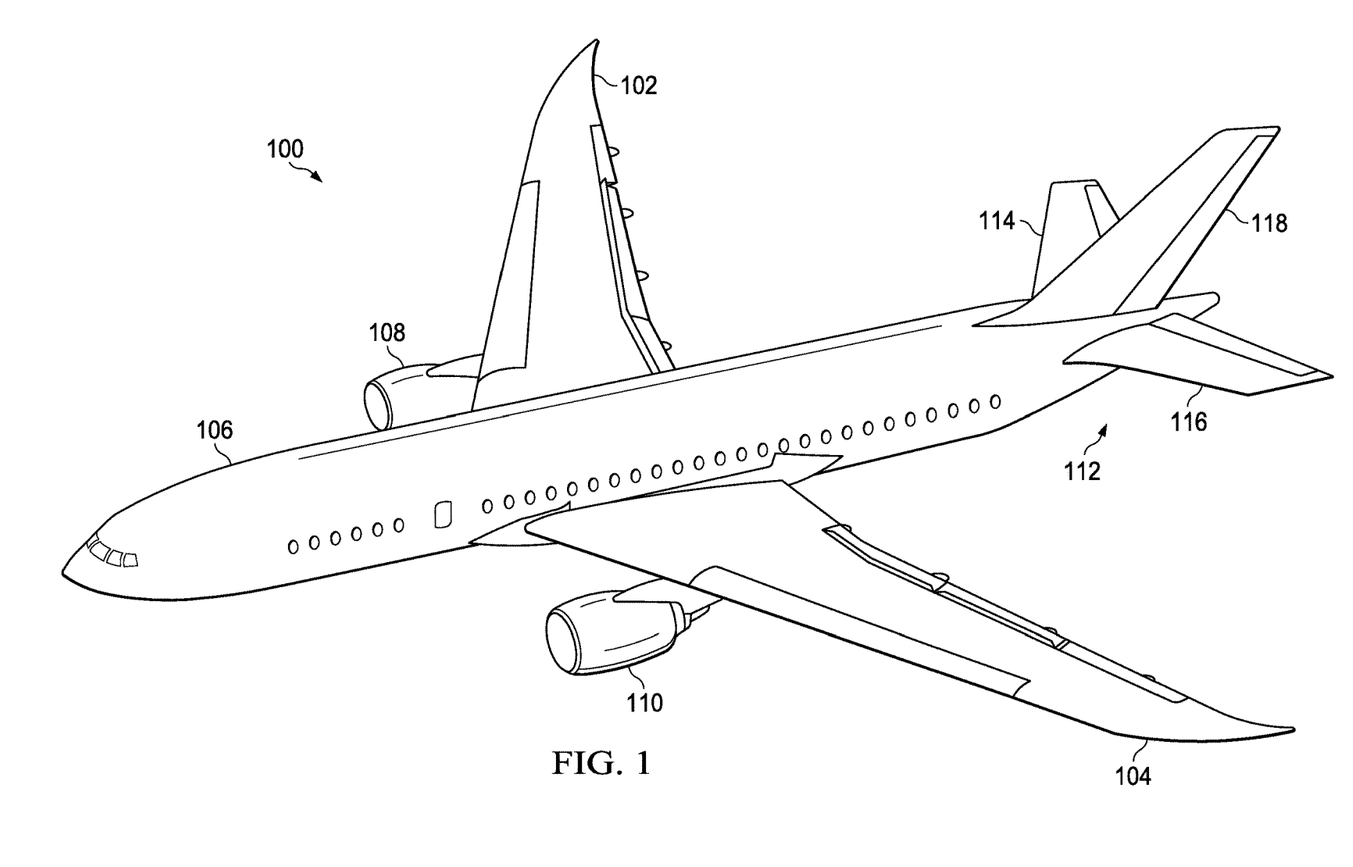
FIG. 1 is an illustration of an aircraft in which an illustrative embodiment may be implemented.

Referring now to the figures and, in particular, with reference to FIG. 1, an illustration of an aircraft is depicted in which an illustrative embodiment may be implemented. In this illustrative example, aircraft 100 has wing 102 and wing 104 connected to body 106. Aircraft 100 includes engine 108 connected to wing 102 and engine 110 connected to wing 104.

Body 106 has tail section 112. Horizontal stabilizer 114, horizontal stabilizer 116, and vertical stabilizer 118 are connected to tail section 112 of body 106.

Aircraft 100 is an example of an aircraft having parts that may be inspected using a laser inspection system connected to a robotic arm connected to a base of a crane system. For example, during manufacturing, components of at least one of wing 102, wing 104, body 106, or tail section 112 may be inspected using the described method and system for automated data collection and part validation.

As used herein, the phrase "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, "at least one of item A, item B, or item C" may include, without limitation, item A, item A and item B, or item B. This example also may include item A, item B, and item C or item B and item C. Of course, any combination of these items may be present. In other examples, "at least one of" may be, for example, without limitation, two of item A; one of item B; and ten of item C; four of item B and seven of item C; or other suitable combinations.

This illustration of aircraft 100 is provided for purposes of illustrating one environment in which the different illustrative embodiments may be implemented. The illustration of aircraft 100 in FIG. 1 is not meant to imply architectural limitations as to the manner in which different illustrative embodiments may be implemented. For example, aircraft 100 is shown as a commercial passenger aircraft. The different illustrative embodiments may be applied to other types of aircraft, such as a private passenger aircraft, a rotorcraft, or other suitable types of aircraft.

Although the illustrative examples for an illustrative embodiment are described with respect to an aircraft, the illustrative embodiments may be applied to other types of structures. The structure may be, for example, a mobile structure, a stationary structure, a land-based structure, an aquatic-based structure, or a space-based structure. More specifically, the structure may be a surface ship, a tank, a personnel carrier, a train, a spacecraft, a space station, a satellite, a submarine, a manufacturing facility, a building, or other suitable structures.

Figure 2:
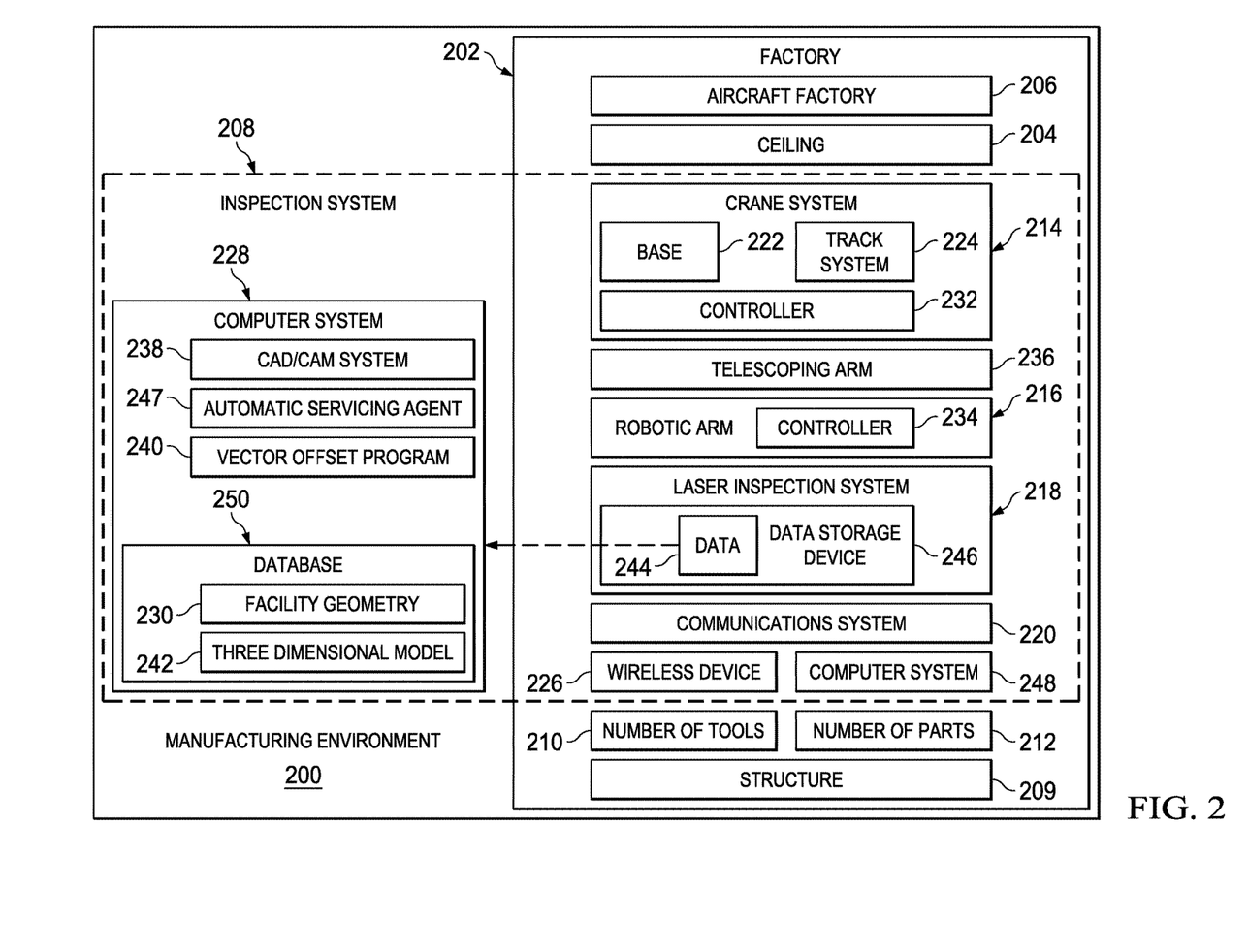
FIG. 2 is an illustration of a block diagram of a manufacturing environment in accordance with an illustrative embodiment.

Turning now to FIG. 2, an illustration of a block diagram of a manufacturing environment is depicted in accordance with an illustrative embodiment. Manufacturing environment 200 includes factory 202 having ceiling 204. In some illustrative examples, factory 202 may be aircraft factory 206. Components of aircraft 100 of FIG. 1 may be manufactured in aircraft factory 206.

Inspection system 208 associated with factory 202 inspects structures, such as structure 209 within factory 202. Number of tools 210 and number of parts 212 are present within factory 202. Structure 209 takes the form of one of a tool of number of tools 210 or a part of number of parts 212. As used herein, "a number of," when used with reference to items, means one or more items. Thus, "number of tools" 210 includes one or more tools. Likewise, "number of parts" 212 includes one or more parts.

Number of tools 210 is used in the manufacturing and processing of number of parts 212. Number of tools 210 includes any desirable size or shape of tools. The location of number of tools 210 within factory 202 may change during the manufacturing. For example, a tool of number of tools 210 may be moved within factory 202 to manufacture a part of number of parts 212. The quantity of tools in number of tools 210 may change during the manufacturing. The tools may be moved into or out of factory 202 as needed.

Number of parts 212 includes any desirable size or shape of parts. In some illustrative examples, number of parts 212 includes any desirable components of aircraft 100 of FIG. 1. For example, number of parts 212 may include components of at least one of wing 102, wing 104, body 106, or tail section 112 of aircraft 100 of FIG. 1.

As depicted, some components of inspection system 208 are located within factory 202. Inspection system 208 includes crane system 214, robotic arm 216, laser inspection system 218, and communications system 220. Robotic arm 216 is a six-axis, one hundred and fifty degree articulating arm. Robotic arm 216 is connected to base 222 of crane system 214.

As used herein, a first component "connected to" a second component means that the first component can be connected directly or indirectly to the second component. In other words, additional components may be present between the first component and the second component. The first component is considered to be indirectly connected to the second component when one or more additional components are present between the two components. When the first component is directly connected to the second component, no additional components are present between the two components.

Laser inspection system 218 is connected to robotic arm 216. In some illustrative examples, laser inspection system 218 is directly connected to the end of robotic arm 216. Communications system 220 is configured to send and receive instructions for crane system 214, robotic arm 216, and laser inspection system 218.

Robotic arm 216 has desirable functional capabilities. The functional capabilities include desirable motion of travel and desirable axis and rotation capabilities.

The desirable motion of travel may be dependent on the size of factory 202. In some examples, robotic arm 216 has Z-axis motion of travel of −12 feet to +12 feet; Y-axis motion of travel of +20 feet in both directions; and X-axis motion of travel of +20 feet in both directions.

The desirable axis and rotation capabilities are independent of size of factory 202. Robotic arm 216 desirably has an X-Y yaw axis capability of +/−180 degrees; a Y-Z pitch axis capability of +/−115 degrees; and an X-Z rotation capability of at least +/−150 degrees.

In some examples, crane system 214 includes track system 224. Track system 224 may be positioned within factory 202 using any desirable method. In some examples, track system 224 is connected to ceiling 204 of factory 202. Base 222 of crane system 214 travels in at least one of an x-direction or a y-direction within manufacturing environment 200 along track system 224.

Inspection system 208 also includes wireless device 226. Wireless device 226 may take a number of different forms. Depending on the implementation, wireless device 226 may be selected from one of a laptop, a smartphone, a personal digital assistant, a tablet, a portable computer, an external storage device, or some other type of portable device capable of storing a sufficiently large amount of data.

Wireless device 226 is configured to activate movement of at least one of crane system 214 or robotic arm 216 for inspection of a structure using laser inspection system 218. Wireless device 226 may activate movement of at least one of crane system 214 or robotic arm 216 directly or indirectly. For example, wireless device 226 may send instructions directly to at least one of crane system 214 or robotic arm 216 to activate movement. As another example, wireless device 226 may activate movement by sending a request to computer system 228, and computer system 228 sending instructions to at least one of crane system 214 or robotic arm 216.

In some examples, wireless device 226 is configured to send movement instructions generated based on operator input. The operator input may be received by using a screen, keypad, tracking device, or any other desirable type of input device.

In one illustrative example, an operator may "drive" at least one of crane system 214 or robotic arm 216 using wireless device 226. In this example, the operator may manually control a path of crane system 214 or robotic arm 216 using wireless device 226 as a controller. Wireless device 226 may generate the movement instructions for at least one of crane system 214 or robotic arm 216 as user input is received at wireless device 226.

In another illustrative example, wireless device 226 may generate the movement instructions based on the operator's selection. For example, the operator may select a type of part, a type of inspection, or any other desirable type of input from a menu. Wireless device 226 may generate the movement instructions based on this menu input.

In yet another illustrative example, wireless device 226 is configured to trigger generation of the movement instructions for at least one of crane system 214 or robotic arm 216 by computer system 228 based on facility geometry 230. Facility geometry 230 includes at least one of positions of number of tools 210 within factory 202, shapes and sizes of number of tools 210, positions of number of parts 212 within factory 202, shapes and sizes of number of parts 212, or a shape and size of factory 202. By using facility geometry 230 to generate the movement instructions, crane system 214 and robotic arm 216 avoid undesirable contact with components of factory 202, number of parts 212, and number of tools 210. After generation of the movement instructions by either wireless device 226 or computer system 228, communications system 220 sends the movement instructions.

Communications system 220 includes a plurality of communication components configured to communicate with other devices. The plurality of communication components may provide communications using physical communications links, wireless communications links, or both. Communications system 220 includes communication components associated with at least one of crane system 214, robotic arm 216, laser inspection system 218, wireless device 226, and computer system 228.

Components of communications system 220 are configured to send and receive wireless signals in a range of 400-650 mHz to send and receive instructions for crane system 214. For example, a receiver associated with crane system 214 is configured to receive wireless signals in the range of 400-650 mHz. As another example, at least one of a transmitter associated with computer system 228 or a transmitter associated with wireless device 226 is configured to transmit wireless signals in the range of 400-650 mHz.

The components of communications system 220 are configured to send and receive wireless signals in a range of 2.4-5.0 Ghz to send and receive instructions for robotic arm 216. For example, a receiver associated with robotic arm 216 is configured to receive wireless signals in the range of 2.4-5.0 Ghz. As another example, at least one of a transmitter associated with computer system 228 or a transmitter associated with wireless device 226 is configured to transmit the wireless signals in the range of 2.4-5.0 Ghz.

Controller 232 controls crane system 214 according to instructions received using communications system 220. Controller 234 controls robotic arm 216 according to instructions received using communications system 220. Although controller 232 and controller 234 are shown as separate components, in some illustrative examples, crane system 214 and robotic arm 216 may be controlled using the same controller.

In some examples, inspection system 208 also includes telescoping arm 236. In these examples, robotic arm 216 is connected to base 222 by telescoping arm 236. Telescoping arm 236 is connected to base 222 of crane system 214. In these examples, telescoping arm 236 may be described as directly connected to base 222. Telescoping arm 236 enables robotic arm 216 to move greater distances away from ceiling 204 of factory 202.

Computer system 228 includes computer-aided design/computer-aided manufacturing (CAD/CAM) system 238 configured to generate vector offset program 240 to move robotic arm 216 to inspect structure 209. Vector offset program 240 is a set of instructions for robotic arm 216. Computer-aided design/computer-aided manufacturing system 238 uses at least one of facility geometry 230 or three-dimensional model 242 of structure 209 to form vector offset program 240. In some illustrative examples, vector offset program 240 includes instructions for movement of robotic arm 216 during inspection of structure 209 by laser inspection system 218. Vector offset program 240 uses location and shape data from facility geometry 230 to avoid undesirable contact of components of inspection system 208 with components of factory 202, number of parts 212, or number of tools 210.

During inspection, laser inspection system 218 forms data 244. Data 244 is stored in data storage device 246 until inspection of structure 209 is completed. When inspection of structure 209 is completed, data 244 is sent to computer system 228 either automatically or by instruction from wireless device 226.

Computer-aided design/computer-aided manufacturing system 238 is further configured to compare data 244 generated by laser inspection system 218 for structure 209 to three-dimensional model 242 of structure 209. Automatic servicing agent 247 starts an internal program within computer-aided design/computer-aided manufacturing system 238 to interrogate data 244 to three-dimensional model 242. If the results of this interrogation are within tolerance, structure 209 is validated.

Computer system 228 may be configured to perform other functions. In some examples, computer system 228 is configured to generate a program to drive base 222 of crane system 214 towards structure 209 within manufacturing environment 200 to be inspected based on facility geometry 230.

Facility geometry 230 may be referred to as geo-spatial location geometry. The geo-spatial location geometry may be in the form of (deg-min-sec)—latitude and longitude or in the form of ASCII-based X-Y axis geometry. Facility geometry 230 may be used for X-Y axis positioning for crane system 214 and providing association to the robot scanning geometry which provides X,Y,Z, and I,J,K values for robotic arm 216.

The X-Y axis positioning geometry for crane system 214 goes through data conversion to XML and is sent to a wireless supervisory control and data acquisition (SCADA) service. Following SCADA, instructions are sent to controller 232, also referred to as the crane programmable logic controller (PLC). The crane programmable logic controller drives crane system 214 using a numerically based drive program -X-Y axis geometry based file program.

The robot scanning geometry X,Y,Z, I,J,K + avoidance geometry for robotic arm 216 goes through data conversion to XML and is sent to controller 234, also referred to as the robot programmable logic controller. The robot programmable logic controller drives robotic arm 216 using a numerically based drive program with -X-YZ, I-J-K values in an ASCII format.

The illustration of manufacturing environment 200 in FIG. 2 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, although computer-aided design/computer-aided manufacturing (CAD/CAM) system 238 is depicted as on computer system 228 outside of factory 202, in some illustrative examples, computer-aided design/computer-aided manufacturing (CAD/CAM) system 238 may instead be associated with computer system 248 within factory 202. Further, although facility geometry 230 and three-dimensional model 242 are depicted as within database 250, in some illustrative examples, facility geometry 230 and three-dimensional model 242 may be present in separate databases.

Figure 3:
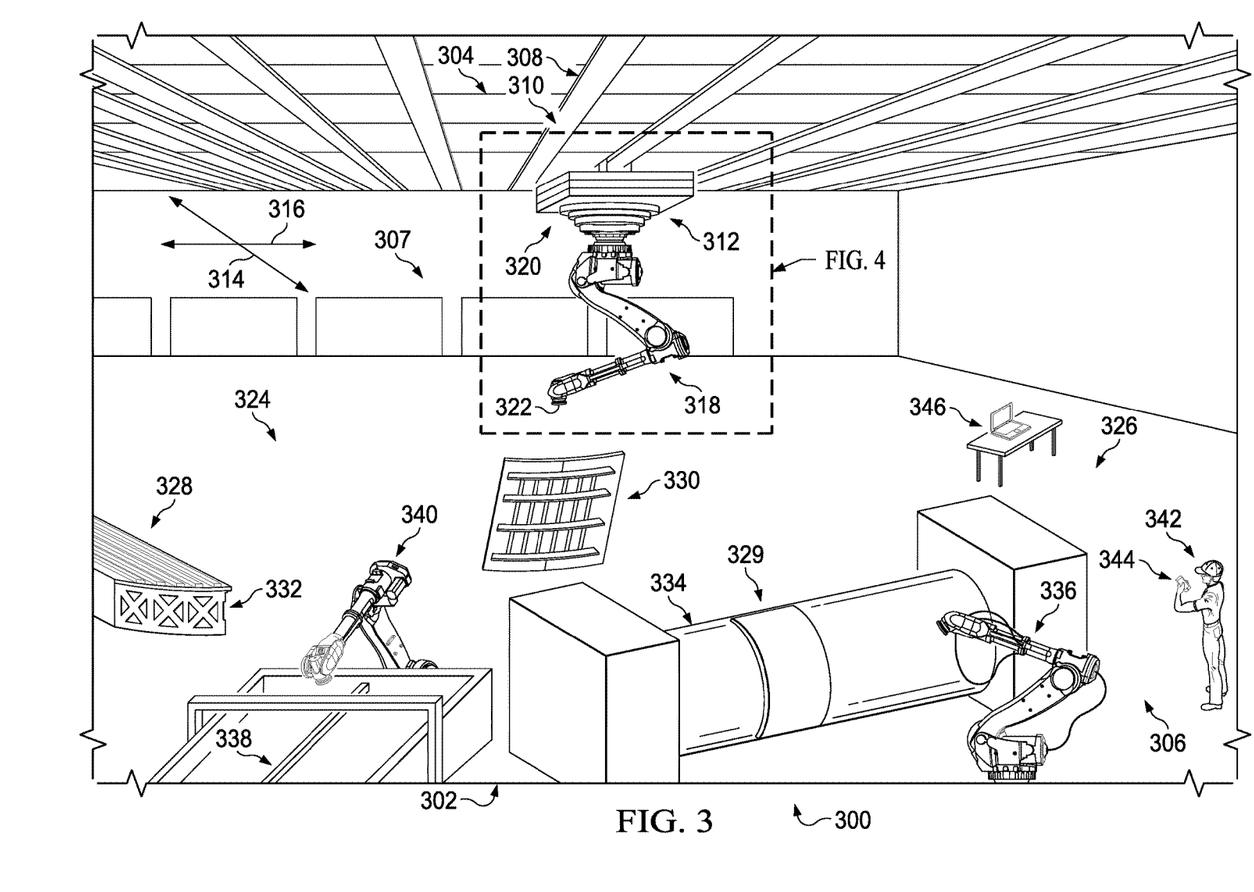
FIG. 3 is an illustration of a perspective view of a manufacturing environment employing an inspection system, wherein an aircraft is being assembled in accordance with an illustrative embodiment.

Turning now to FIG. 3, an illustration of a perspective view of a manufacturing environment employing an inspection system, wherein an aircraft is being assembled is depicted in accordance with an illustrative embodiment. Manufacturing environment 300 may be a physical implementation of manufacturing environment 200 of FIG. 2.

Manufacturing environment 300 includes factory 302 having ceiling 304 and floor 306. As depicted, factory 302 is an aircraft factory. Inspection system 307 is present within manufacturing environment 300.

As depicted, track system 308 of crane system 310 is connected to ceiling 304. Base 312 of crane system 310 may move along track system 308 in at least one of x-direction 314 or y-direction 316.

Robotic arm 318 is connected to base 312 by telescoping arm 320. Laser inspection system 322 for inspecting at least one of number of parts 324 and number of tools 326 within manufacturing environment 300 is connected to robotic arm 318. Laser inspection system 322 generates data while at least one of robotic arm 318 or base 312 of crane system 310 moves within factory 302.

As depicted, number of parts 324 includes stringers 328, composite panel 329, and assembled panels 330. Number of parts 324 present in factory 302 may change during manufacturing of an aircraft. Further, the location of each part of number of parts 324 present in factory 302 may change during manufacturing of the aircraft. As depicted, stringers 328 are resting on table 332. However, stringers 328 may be used to form a panel similar to assembled panels 330. Any of number of parts 324 may be inspected using inspection system 307.

As depicted, number of tools 326 includes jig 334, tape laying robot 336, jig 338, and tape laying robot 340. Tape laying robot 336 applies composite tape to jig 334 to form composite panel 329. Tape laying robot 340 applies composite tape to jig 338 to form a stringer, such as stringers 328. Number of tools 326 present in factory 302 may change during manufacturing of the aircraft. Further, the location of each tool of number of tools 326 present in factory 302 may change during manufacturing of the aircraft. Any of number of tools 326 may be inspected using inspection system 307. For example, jig 334 or jig 338 may be inspected for appropriate shape, size, or location within factory 302.

Operator 342 triggers inspection of a structure using wireless device 344. The structure may be at least one of a part of number of parts 324 or a tool of number of tools 326. In some illustrative examples, operator 342 may indicate a structure to be inspected using input on wireless device 344. One of wireless device 344 or computer system 346 sends movement instructions to at least one of crane system 310 or robotic arm 318. In some illustrative examples, computer system 346 creates movement instructions based on input of operator 342 and known facility geometry. In other illustrative examples, operator 342 may manually drive inspection system 307 using wireless device 344.

After inspection, laser inspection system 322 sends data to computer system 346 for analysis. Computer system 346 compares the data to a three-dimensional model of the structure. Afterwards, results are provided in a desirable format. If the results are within tolerance, the inspected structure is validated.

Figure 4:
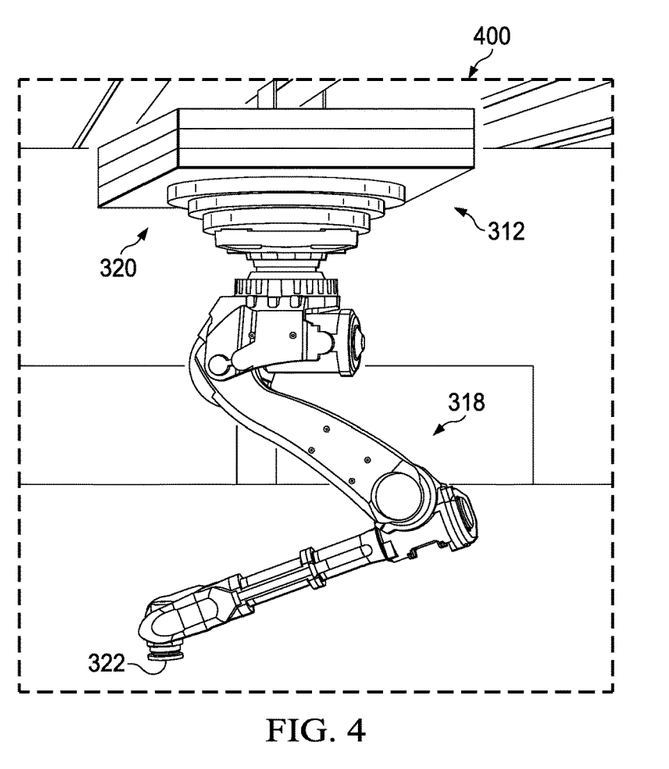
FIG. 4 is an illustration of a robotic arm and a telescoping arm connected to a crane of a manufacturing environment in accordance with an illustrative embodiment.

Turning now to FIG. 4, an illustration of a robotic arm and a telescoping arm connected to a crane of a manufacturing environment is depicted in accordance with an illustrative embodiment. View 400 is a view of manufacturing environment 300 of FIG. 3 within box 4-4. View 400 provides a closer look at components of inspection system 307 of FIG. 3.

Figure 5:
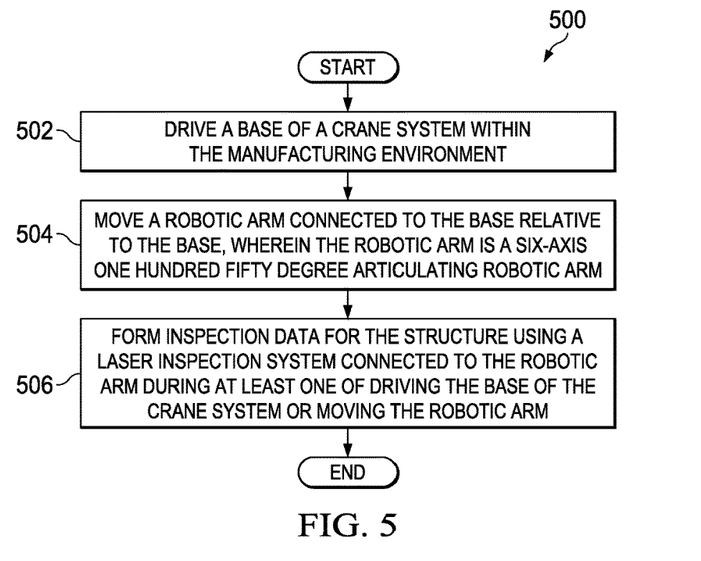
FIG. 5 is an illustration of a flowchart of a method for inspecting a structure in a manufacturing environment in accordance with an illustrative embodiment.

Turning now to FIG. 5, an illustration of a flowchart of a method for inspecting a structure in a manufacturing environment is depicted in accordance with an illustrative embodiment. Method 500 may be used to inspect structure 209 in manufacturing environment 200 of FIG. 2. Method 500 may be used to inspect a part of number of parts 324 or a tool of number of tools 326 in manufacturing environment 300 of FIG. 3.

Method 500 drives a base of a crane system within the manufacturing environment (operation 502). Method 500 moves a robotic arm connected to the base relative to the base, wherein the robotic arm is a six-axis, one hundred and fifty degree articulating robotic arm (operation 504). Method 500 forms inspection data for the structure using a laser inspection system connected to the robotic arm during at least one of driving the base of the crane system or moving the robotic arm (operation 506). Afterwards the process terminates.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

In some illustrative examples, method 500 further generates instructions for at least one of driving the base of the crane system or moving the robotic arm based on facility geometry stored on a computer system. In other illustrative examples, method 500 further generates instructions for at least one of driving the base of the crane system or moving the robotic arm based on user input received on a wireless device. In some illustrative examples, method 500 compares inspection data for the structure to a three-dimensional model of the structure to form results. In other illustrative examples, method 500 changes a length of a telescoping arm positioned between the robotic arm and the base of the crane system. In some examples, method 500 disables manual crane controls prior to driving the base of the crane or moving the robotic arm.

Figure 6:
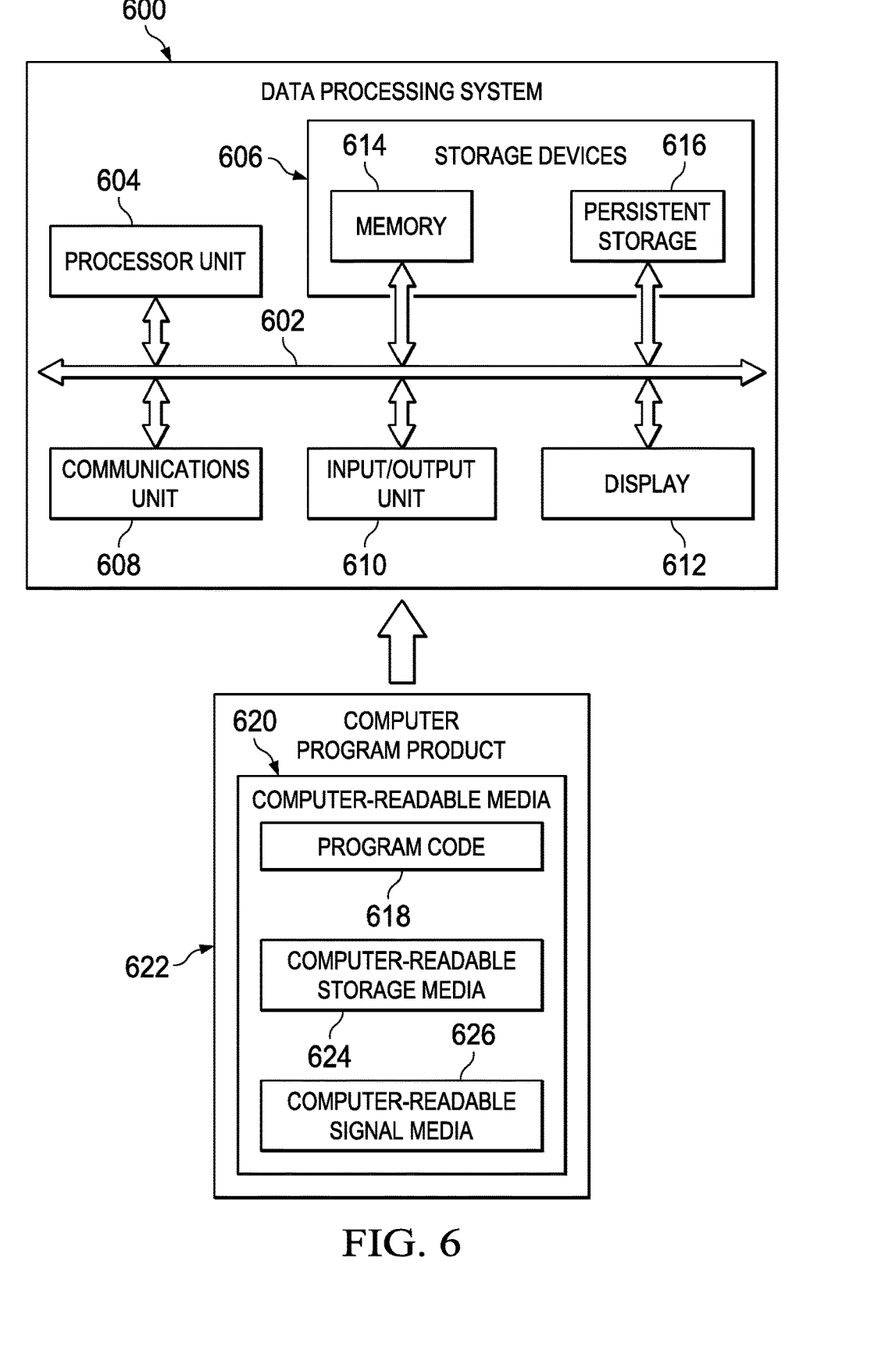
FIG. 6 is an illustration of a block diagram of a data processing system in accordance with an illustrative embodiment.

Turning now to FIG. 6, an illustration of a block diagram of a data processing system is depicted in accordance with an illustrative embodiment. Data processing system 600 may be used to implement portions of inspection system 208 of FIG. 2, such as computer system 228 or computer system 248. As depicted, data processing system 600 includes communications framework 602, which provides communications between processor unit 604, storage devices 606, communications unit 608, input/output unit 610, and display 612. In some cases, communications framework 602 may be implemented as a bus system.

Processor unit 604 is configured to execute instructions for software to perform a number of operations. Processor unit 604 may comprise a number of processors, a multi-processor core, and/or some other type of processor, depending on the implementation. In some cases, processor unit 604 may take the form of a hardware unit, such as a circuit system, an application specific integrated circuit (ASIC), a programmable logic device, or some other suitable type of hardware unit.

Instructions for the operating system, applications, and/or programs run by processor unit 604 may be located in storage devices 606. Storage devices 606 may be in communication with processor unit 604 through communications framework 602. As used herein, a storage device, also referred to as a computer-readable storage device, is any piece of hardware capable of storing information on a temporary and/or permanent basis. This information may include, but is not limited to, data, program code, and/or other information.

Memory 614 and persistent storage 616 are examples of storage devices 606. Memory 614 may take the form of, for example, a random access memory or some type of volatile or non-volatile storage device. Persistent storage 616 may comprise any number of components or devices. For example, persistent storage 616 may comprise a hard drive, a flash memory, a rewritable optical disk, a rewritable magnetic tape, or some combination of the above. The media used by persistent storage 616 may or may not be removable.

Communications unit 608 allows data processing system 600 to communicate with other data processing systems and/or devices. Communications unit 608 may provide communications using physical and/or wireless communications links.

Input/output unit 610 allows input to be received from and output to be sent to other devices connected to data processing system 600. For example, input/output unit 610 may allow user input to be received through a keyboard, a mouse, and/or some other type of input device. As another example, input/output unit 610 may allow output to be sent to a printer connected to data processing system 600.

Display 612 is configured to display information to a user. Display 612 may comprise, for example, without limitation, a monitor, a touch screen, a laser display, a holographic display, a virtual display device, and/or some other type of display device.

In this illustrative example, the processes of the different illustrative embodiments may be performed by processor unit 604 using computer-implemented instructions. These instructions may be referred to as program code, computer usable program code, or computer-readable program code and may be read and executed by one or more processors in processor unit 604.

In these examples, program code 618 is located in a functional form on computer-readable media 620, which is selectively removable, and may be loaded onto or transferred to data processing system 600 for execution by processor unit 604. Program code 618 and computer-readable media 620 together form computer program product 622. In this illustrative example, computer-readable media 620 may be computer-readable storage media 624 or computer-readable signal media 626.

Computer-readable storage media 624 is a physical or tangible storage device used to store program code 618, rather than a medium that propagates or transmits program code 618. Computer-readable storage media 624 may be, for example, without limitation, an optical or magnetic disk or a persistent storage device that is connected to data processing system 600.

Alternatively, program code 618 may be transferred to data processing system 600 using computer-readable signal media 626. Computer-readable signal media 626 may be, for example, a propagated data signal containing program code 618. This data signal may be an electromagnetic signal, an optical signal, and/or some other type of signal that can be transmitted over physical and/or wireless communications links.

Figure 7:
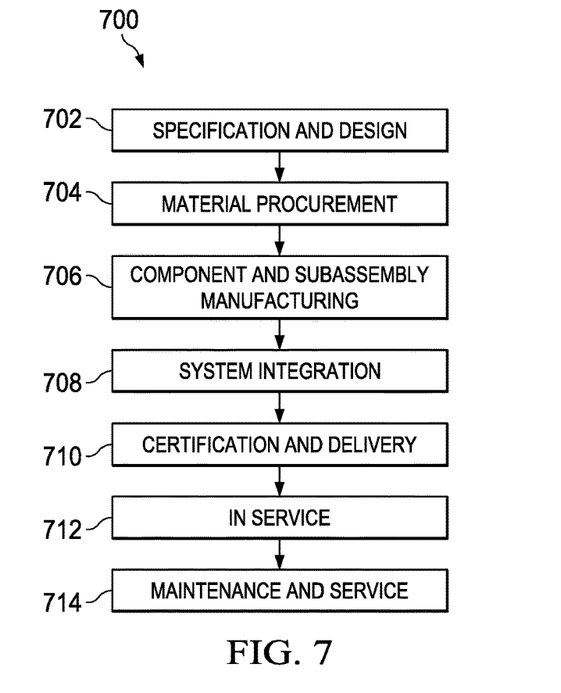
FIG. 7 is an illustration of an aircraft manufacturing and service method in the form of a block diagram in accordance with an illustrative embodiment.
Figure 8:
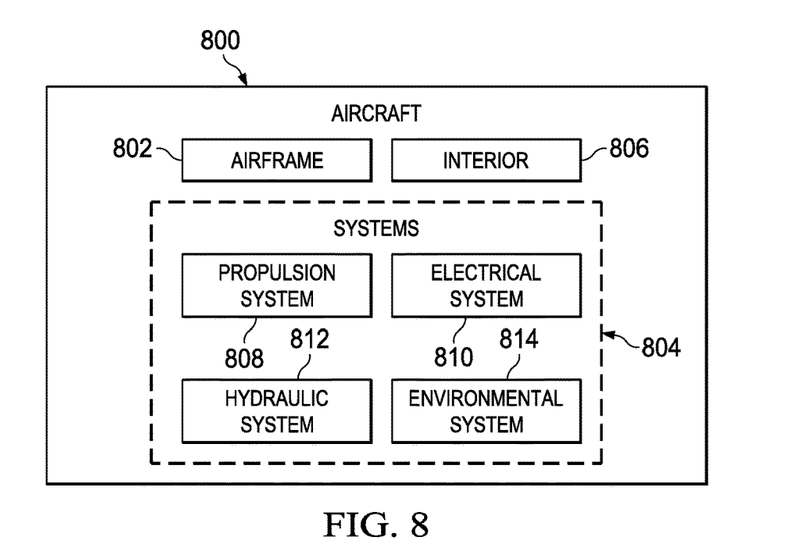
FIG. 8 is an illustration of an aircraft in the form of a block diagram in which an illustrative embodiment may be implemented.

Illustrative embodiments of the present disclosure may be described in the context of aircraft manufacturing and service method 700 as shown in FIG. 7 and aircraft 800 as shown in FIG. 8. Turning first to FIG. 7, an illustration of an aircraft manufacturing and service method is depicted in accordance with an illustrative embodiment. During preproduction, aircraft manufacturing and service method 700 may include specification and design 702 of aircraft 800 in FIG. 8 and material procurement 704.

During production, component and subassembly manufacturing 706 and system integration 708 of aircraft 800 takes place. Thereafter, aircraft 800 may go through certification and delivery 710 in order to be placed in service 712. While in service 712 by a customer, aircraft 800 is scheduled for routine maintenance and service 714, which may include modification, reconfiguration, refurbishment, and other maintenance or service.

Each of the processes of aircraft manufacturing and service method 700 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 8, an illustration of an aircraft is depicted in which an illustrative embodiment may be implemented. In this example, aircraft 800 is produced by aircraft manufacturing and service method 700 in FIG. 7 and may include airframe 802 with plurality of systems 804 and interior 806. Examples of systems 804 include one or more of propulsion system 808, electrical system 810, hydraulic system 812, and environmental system 814. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 700. One or more illustrative embodiments may be used during component and subassembly manufacturing 706 of FIG. 7. For example, inspection system 208 of FIG. 2 may be used to inspect parts during component and subassembly manufacturing 706. Further, inspection system 208 of FIG. 2 may be used to inspect replacement parts during maintenance and service 714 of FIG. 7.

An operational concept of the inspection system is that facilities will permanently bolt the robotic arm and the telescoping arm to the base plate of the crane system on the factory ceiling. Facilities will then attach the control cabling from the robotic arm to the crane control system. An operator will then download a numeric control (NC) offset measurement tracking program and run the robot with a handheld wireless device. Once the process is complete, the robotic arm and the telescoping arm may then rotate back into a protective box. After the storage process is complete, data will be transmitted either to the product data manager via a handheld wireless device for an automated interrogation process to occur or through a persistent gateway for data analytics processing. The results of the data analytics processing will automatically be posted to an internally based website for review by the customer.

The systems concept of the inspection system is that a six-axis, one hundred and fifty degree articulating robotic arm will be numerically driven through large tooling structures by an NC vector offset program developed on the computer-aided design/computer-aided manufacturing (CAD/CAM) system. This robot will have a digital laser scanner on the end effector of the robotic arm. The laser scanner will record and cache all of the identified point and vector details onto an external hard drive. The operator may then use a specific handheld device to perform a wireless data transfer from the laser tracker external hard drive to a specific folder within the PDM database where an automatic servicing agent (ASA) will start an internal program within the CAD/CAM system to interrogate the data file to the computer-aided design (CAD) geometry.

In some examples, the wireless data transfer may be performed automatically without the operator. The results of the interrogation will be written to a database into a web-based hypertext mark-up language (HTML) formatted flat file and then automatically sent to an internally secure website. Users can then log into this website and type in a part number to review the results of the measurement on the associated tooling or the data analytics.

The inspection system will automate the conventionally manual tooling inspection certification process on thousands of large, out-sized aircraft assembly tools and jigs in large manufacturing factories and provide web-based data interrogation results and visibility to the users with desirable accuracy and efficiency.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An inspection system comprising:
a crane system;
a six-axis articulating robotic arm, wherein the robotic arm is connected to a base of the crane system;
a laser inspection system connected to the robotic arm;
a communications system configured to send and receive instructions for the crane system, the robotic arm, and the laser inspection system; and
a wireless device configured to activate movement of at least one of the crane system or the robotic arm for inspection of a structure using the laser inspection system, wherein the wireless device is configured to send movement instructions generated based on operator input selected from a menu of options, and wherein the options comprise one of a type of part and a type of inspection.

2. The inspection system of claim 1, wherein the crane system comprises a track system, wherein the base of the crane system travels in at least one of an x-direction or a y-direction within a manufacturing environment along the track system.

3. The inspection system of claim 1, wherein the wireless device is configured to trigger generation of movement instructions for at least one of the crane system or the robotic arm by a computer system based on facility geometry.

4. The inspection system of claim 1, wherein the robotic arm is connected to the base by a telescoping arm.

5. The inspection system of claim 1, wherein components of the communications system are configured to send and receive wireless signals in a range of 400-650 mHz to send and receive instructions for the crane system.

6. The inspection system of claim 1, wherein components of the communications system are configured to send and receive wireless signals in a range of 2.4-5.0 Ghz to send and receive instructions for the robotic arm.

7. An inspection system comprising:
a crane system having a base and a track system, wherein the base of the crane system travels in at least one of an x-direction or a y-direction in a manufacturing environment along the track system;
a telescoping arm connected to the base of the crane system;
a six-axis articulating robotic arm connected to the telescoping arm;
a laser inspection system connected to the robotic arm;
a wireless device configured to activate movement of at least one of the crane system, the telescoping arm, or the robotic arm for inspection of a structure within the manufacturing environment by the laser inspection system, wherein movement instructions for movement of the at least one of the crane system, the telescoping arm, or the robotic arm are generated based on operator input selected from a menu of options wherein the options comprise one of a type of part and a type of inspection; and
a communications system configured to send and receive instructions for the crane system, the robotic arm, and the laser inspection system.

8. The inspection system of claim 7 further comprising:
a computer-aided design/computer-aided manufacturing system configured to generate a vector offset program to move the robotic arm to inspect a structure.

9. The inspection system of claim 8, wherein the computer-aided design/computer aided manufacturing system is further configured to compare data generated by the laser inspection system for the structure to a three-dimensional model of the structure.

10. The inspection system of claim 7, wherein a computer system is configured to generate a program to drive the base of the crane system towards a structure within the manufacturing environment to be inspected based on facility geometry.

11. The inspection system of claim 7, wherein the wireless device is configured to send movement instructions generated based on operator input.

12. The inspection system of claim 7, wherein the wireless device is configured to trigger generation of movement instructions for at least one of the crane system or the robotic arm by a computer system based on facility geometry.

13. A method of inspecting a structure in a manufacturing environment, the method comprising:
driving a base of a crane system within the manufacturing environment;
moving a robotic arm connected to the base relative to the base, wherein the robotic arm is an articulating robotic arm; and
forming inspection data for the structure using a laser inspection system connected to the robotic arm during at least one of driving the base of the crane system or moving the robotic arm; and
generating instructions for at least one of driving the base of the crane system or moving the robotic arm based on user input received on a wireless device, wherein the instructions are generated based on operator input selected from a menu of options, and wherein the options comprise one of a type of part and a type of inspection.

14. The method of claim 13 further comprising:
generating instructions for at least one of driving the base of the crane system or moving the robotic arm based on facility geometry stored on a computer system.

15. The method of claim 13 further comprising:
comparing inspection data for the structure to a three-dimensional model of the structure to form results.

16. The method of claim 13 further comprising:
changing a length of a telescoping arm positioned between the robotic arm and the base of the crane system.

17. The method of claim 13 further comprising:
disabling manual crane controls prior to driving the base of the crane system or moving the robotic arm.

* * * * *